United States Patent
Bao et al.

(10) Patent No.: US 7,983,931 B2
(45) Date of Patent: Jul. 19, 2011

(54) SYSTEM AND METHOD FOR CUSTOMIZING WORKFLOW USING STANDARD FORMATS FOR INFORMATION TRANSFER

(75) Inventors: Yongjian Bao, Vernon Hills, IL (US); Thanjavur N. Viswanathan, New Berlin, WI (US); Marie-José Lacroix, Paris (FR); Khaldoun A. Rai, Round Lake, IL (US); Andrew Sorrentino, Northbrook, IL (US)

(73) Assignee: General Electric Company, Schenectady, NY (US)

( * ) Notice: Subject to any disclaimer, the term of this patent is extended or adjusted under 35 U.S.C. 154(b) by 1727 days.

(21) Appl. No.: 10/995,877

(22) Filed: Nov. 23, 2004

(65) Prior Publication Data

US 2006/0111935 A1    May 25, 2006

(51) Int. Cl.
G06Q 10/00 (2006.01)
G06F 19/00 (2011.01)
(52) U.S. Cl. .............................. 705/2; 705/3
(58) Field of Classification Search ............... 705/2–3; 713/161; 600/437
See application file for complete search history.

(56) References Cited

U.S. PATENT DOCUMENTS

| | | | |
|---|---|---|---|
| 6,287,257 B1* | 9/2001 | Matichuk | 600/437 |
| 6,574,629 B1* | 6/2003 | Kaufman et al. | 1/1 |
| 7,028,182 B1* | 4/2006 | Killcommons | 713/161 |
| 2003/0187689 A1* | 10/2003 | Barnes et al. | 705/2 |
| 2005/0096942 A1* | 5/2005 | Shachor | 705/2 |

OTHER PUBLICATIONS

"DICOM Modality Worklist: An Essential Component in a PACS Environment", M. Elon Gale and Daniel R. Gale, Journal of Digital Imaging, vol. 13, No. 3, Aug. 2000, pp. 101-108.*
"Educational RIS/PACS Simulator", Z. Zhou, Maria Law, H.K. Huang, F. Cao, B. Liu, J. Zhang, G. Mogel, J. Zhuang, Medical Imaging 2003: PACS and Integrated Medical Information Systems: Design and Evaluation, Proceedings of SPIE vol. 5033 (2003).*
"HIS/RIS/PACS Integration: Getting to the Gold Standard", Stephen S. Boochever, Radiology Management, May/Jun. 2004.*
"Interfacing the PACS and the HIS: Results of a 5-Year Implementation", Thomas V. Kinsey, Maria C. Horton, Tom E. Lewis, RadioGraphics, May/Jun. 2000, vol. 20, pp. 883-891.*
"The VA's Use of DICOM to Integrate Image Data Seamlessly in to the Online Patient Record", Peter M. Kuzmak and Ruth E. Dayhoff, Proceedings of AMIA Symposium, 1999, pp. 92-96.*

* cited by examiner

*Primary Examiner* — Luke Gilligan
*Assistant Examiner* — Joseph Burgess
(74) *Attorney, Agent, or Firm* — McAndrews, Held & Malloy, Ltd.; Michael A. Dellapenna

(57) ABSTRACT

Embodiments of the present system and method relate generally to standardized electronic communications in a healthcare setting. Certain embodiments of the system include a healthcare information acquisition and management system capable of using information that conforms to an industry standard format for information transfer, an order scheduling system capable of managing information flow within the healthcare setting, and a gateway system interconnecting the healthcare information acquisition and management system and the order scheduling system. In certain embodiments, the gateway system provides for a transfer of nonconforming information between the order scheduling system and the healthcare information acquisition and management system.

13 Claims, 3 Drawing Sheets

SYSTEM AND METHOD FOR CUSTOMIZING WORKFLOW USING STANDARD FORMATS FOR INFORMATION TRANSFER

BACKGROUND OF THE INVENTION

Embodiments of the present system and method relate generally to electronic communications in a healthcare setting. Particularly, certain embodiments relate to providing site-specific, customizable data transfer for imaging devices using the Digital Imaging and Communications in Medicine (DICOM) information model.

Clinics, hospitals, and other healthcare facilities have come to rely more and more on computers over the last several decades. In particular, healthcare facilities employ certain types of digital diagnostic imaging modalities, such as computed tomography, magnetic resonance imaging, ultrasound imaging, and X-ray imaging. Many different manufacturers developed digital diagnostic imaging modalities to gather and transmit diagnostic information, and each manufacturer employed a different, sometimes proprietary, way of handling the digital information. The method of handling information is often hardcoded into the digital diagnostic imaging modality, preventing an individual facility from reconfiguring the handling method to make the handling method uniform across a facility's diverse digital diagnostic imaging modalities. Thus, a single facility using imaging modalities manufactured by different vendors, or multiple facilities using different imaging modalities and seeking to share data, faces the possibility of having imaging modalities that produce different image formats.

A facility with imaging modalities producing different image formats is faced with a number of problems. For example, outputs of each imaging modality may be non-uniform, which may create difficulty for storage of images from different systems onto a single media type or a single server type. Additionally, diagnostic images associated with a single patient may be in different imaging formats, preventing easy electronic association of all diagnostic information with a single patient database record. Furthermore, different imaging modalities with different image formats may not be able to share a single scheduling system. That is, healthcare facilities often schedule imaging procedures to multiple and various imaging modalities through a single, centralized scheduling system, which offers the imaging modality certain information specific to a given patient. Thus, different image formats created an obstacle for a centralized data management system.

In response to the problem of different image data formats, The American College of Radiology (ACR) and the National Electrical Manufacturers Association (NEMA) formed a joint committee in 1983 to develop a standard image format. This standard, eventually known as Digital Imaging and Communications in Medicine (DICOM): 1) promoted communication of digital image information, regardless of device manufacturer; 2) facilitated the development and expansion of Picture Archiving and Communication Systems (PACS) that may also interface with other systems of healthcare information; and 3) allowed for the creation of diagnostic information data bases that may be queried by a wide variety of devices distributed geographically.

Recent enhancements in DICOM have made the standard more flexible. For example, DICOM is now applicable to a network environment, where the initial imaging format standards were applicable only to a point-to-point environment. This enhancement is possible because DICOM now supports operation through the industry standard networking protocol known as TCP/IP. In another enhancement, DICOM specifies how devices claiming conformance to the standard will react to the exchange of both commands and data. In doing so, DICOM specifies the semantics of commands and associated data.

Importantly, DICOM introduces explicit information objects, which are elements used in an object-oriented database management environment in contrast with a relational database management environment. The information objects are used not only for images data such as raw image files, graphics, and waveforms, but also for administrative data to be used for creating reports or output printing. For information objects, DICOM specifies an established technique for uniquely identifying any information object. The technique facilitates unambiguous definitions of relationships between objects as they are used throughout a network.

While the adoption of DICOM has made possible many improvements in the way in which imaging modalities communicate information across the network of a healthcare facility, certain limitations still exist. One limitation involves so-called "legacy" computer systems and in particular, legacy scheduling systems.

As mentioned above, healthcare facilities rely on computers to handle the tremendous amount of diagnostic, therapeutic, demographic, and administrative data created in the modern healthcare environment. In order to make the most efficient use of expensive equipment, healthcare facilities rely on scheduling and order-filling systems to regulate the workloads of expensive and high-demand equipment, such as the aforementioned digital diagnostic imaging modalities. Scheduling and order-filling systems create efficiency, for example, by supplying the imaging modality with information from the computer based patient records on the healthcare network that an imaging modality user would otherwise have to enter manually into the imaging modality in order to accurately associate the diagnostic image with the patient being diagnosed.

For example, within a Radiology department of a clinic, hospital, or other healthcare facility, a Radiology Information System (RIS) manages the business and execution of workflow within the department. Workflow is another name for the pool of actions to be taken that originate when a radiologist or other healthcare professional places an order for work to be performed by an imaging modality on a particular patient. In a Radiology department, the imaging modality may be an X-ray imaging device. In order to execute properly the workflow and return the appropriate diagnostic information, the RIS must communicate at minimum the patient's demographic information, the diagnostic procedure information, and the scheduling information to the X-ray imager. The diagnostic information that results from the scheduled imaging procedure must then be linked to the computer based patient record, along with all other pertinent patient information.

Unfortunately, the RIS of a given healthcare system may be a legacy system and not conform to DICOM. The legacy RIS may instead operate on a Health Level Seven (HL-7) based interface, for example. The healthcare facility is then unable to take advantage of the standardization offered by DICOM and must find a solution involving the legacy system. One expensive and unfavorable solution is to replace the entire scheduling system with a conforming system. This solution is unfavorable at least because the system is otherwise entirely suitable, operable, and familiar to the users.

Another solution is to code into the application logic of the RIS a method of communicating with each of the different DICOM-conforming imaging devices on the healthcare system network. The method of coding communication parameters for each imaging device on a network into the individual application logic of a RIS is time-consuming and specific to each device, therefore creating needless risks to the stability of the network and preventing generic application.

Another example of a drawback of the DICOM standard information model is that the standard necessarily prevents some site-specific customization, even in the case where the scheduling system is DICOM compliant. In particular, DICOM creates an entity-relationship model for communicating worklist items. A worklist item has a one-to-one relationship with a real-world object and is related to other objects from the real-world model. Attributes are defined for each entity in the entity-relationship model. For any worklist item request, the set of attributes is available where the attributes are specific to any entity that is necessary to fill the worklist item request. The method of querying the system for the attributes necessary to fill the worklist item request is through the use of keys.

Keys are the heart of the DICOM information exchange system and also the heart of the second limitation, namely a lack of system flexibility. The keys are predefined by DICOM and include items like scheduled procedure step sequence, scheduled station name, requested procedure code, and patient admission ID number. The keys control the identity of the information that may be communicated among schedulers and imaging modalities on the healthcare network. In some cases, information is hard-coded into the logic of the imaging modality by the manufacturer because of the universality of the DICOM standard. Unfortunately, given the increasing complexity of procedures, the explosion of administrative information associated with a given patient, and the increasing number of devices capable of interfacing with the healthcare network, more flexibility is required in order to achieve greater efficiency.

One system currently in use was developed by Mitra and is available through Agfa Healthcare. The Mitra system maps DICOM keys in a query to nonconforming information from a scheduling and/or order-filling system. However, the Mitra system maps a limited number of DICOM query keys. In the case of a legacy system, the few keys are insufficient to overcome the obstacles discussed above. Also, in a communication transaction, additional information about a client is transferred to a server in addition to the object of the query. The Mitra system allows for mapping of only DICOM query keys. Thus, in the case of site-specific customization, the limited number of mappable keys of the Mitra System does not provide sufficient flexibility, nor does the limited number of mappable keys allow for the capture of nonconforming information available on existing networks, such as network address.

There is a need for a system and method for customizable workflow management to provide for the capture of nonconforming information. There is a need for a system and method for integrating legacy systems into an industry standard information format, such as DICOM, with a generic interface rather than a system specific coding solution. There is a need for a system and method for optimizing workflow among conforming systems of a healthcare facility by generically reconfiguring the query system of DICOM, or other industry standard information formats.

BRIEF SUMMARY OF THE INVENTION

Certain embodiments of the present invention provide a customizable information interface system for use in a healthcare setting. Certain embodiments of the system include a healthcare information acquisition and management system capable of using information that conforms to an industry standard format for information transfer, an order scheduling system capable of managing information flow within the healthcare setting, and a gateway system interconnecting the healthcare information acquisition and management system and the order scheduling system. In certain embodiments, the gateway system provides for a transfer of nonconforming information between the order scheduling system and the healthcare information acquisition and management system.

Certain embodiments of a method for providing for information transfer among information systems in a healthcare setting include transforming at least part of a query from a healthcare information acquisition and management system provided in a first format into a second format, transforming at least part of a set of information from an order scheduling system arranged in the first or a third format into the second format, and filling the query from the healthcare information acquisition and management system with the set of information from an order scheduling system.

In an embodiment, a computer readable storage medium includes a set of instructions for a computer directed to managing information workflow. The set of instructions for a computer includes a mapping routine for transforming a query from a healthcare information acquisition and management system from a first format into a second format, a coding routine for transforming data from an order scheduling system from the first format or a third format into the second format, and a query-filling routine for matching data from the order scheduling system with the query from the healthcare information acquisition and management system. The query filling routine uses the second format to accomplish the matching.

Figure 1:
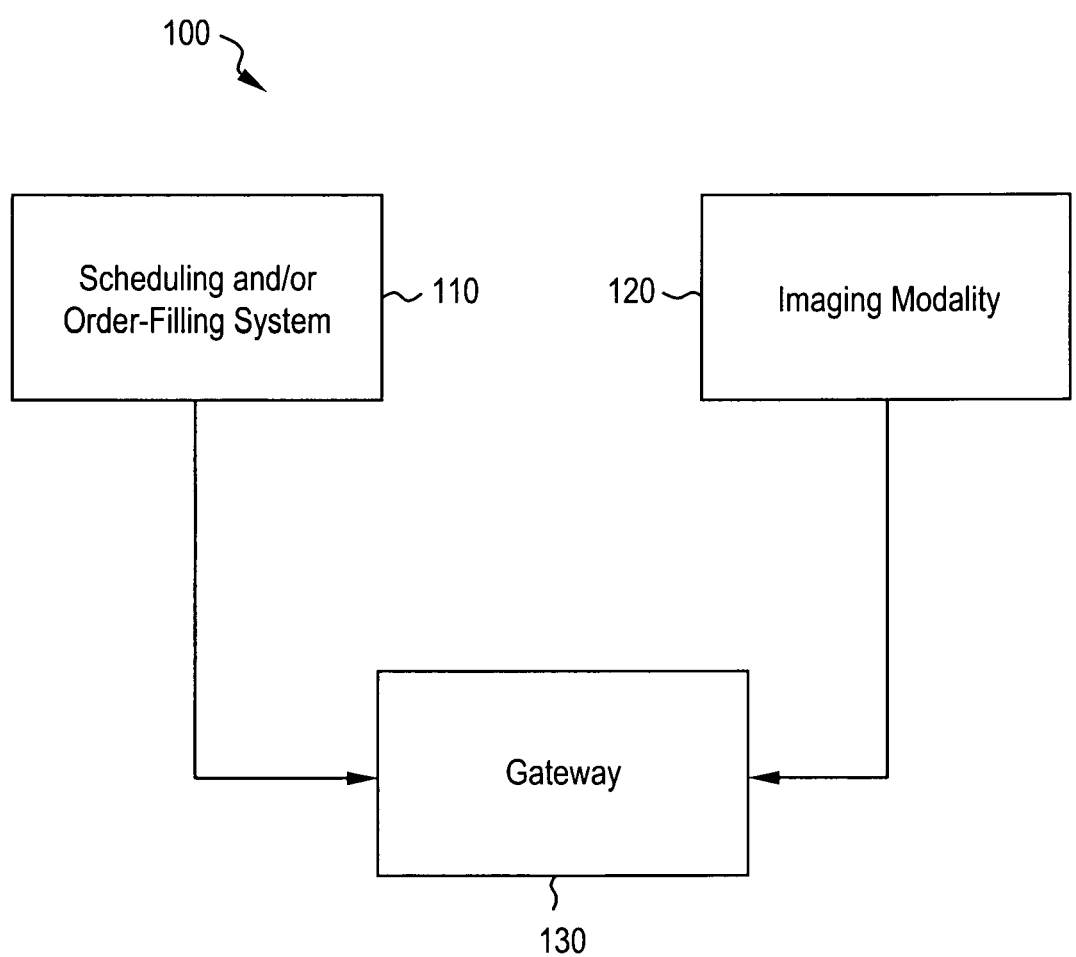
FIG. 1 illustrates a system for the overall flow of information according to an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentalities shown in the attached drawings.

DETAILED DESCRIPTION OF THE INVENTION

FIG. 1 illustrates a system 100, according to one embodiment of the invention, for the overall flow of imaging and imaging-related information in a healthcare setting such as a hospital or clinic. System 100 includes scheduling and/or order-filling system 110, imaging modality 120, and gateway 130. Scheduling and/or order-filling system 110 and imaging modality 120 are interconnected through gateway 130 such that data may flow to and from scheduling and/or order-filling system 110 and imaging modality 120.

Scheduling and/or order-filling system 110 is the system which handles the diagnostic and administrative data for a clinical or hospital department. In the example of a Radiology department, scheduling and/or order-filling system 110 may be a Radiology Information System (RIS). Other examples of systems include a Hospital Information System (HIS), a Clinical Information System (CIS), and a Picture Archive and Communication System (PACS). Typically, the type of data stored on systems like a RIS, HIS, CIS, or PACS includes patient identity and demographics, clinical encounter, imaging diagnostic procedure request, and scheduling and results data.

A user in the hospital or clinical department will use scheduling and/or order-filling system 110 to schedule an imaging procedure on any one of the imaging devices available in the hospital or clinic to diagnose a given patient. In FIG. 1, a single imaging device, imaging modality 120, is shown for the sake of clarity but in practice a hospital or clinic will have various and different imaging devices. Examples of imaging modalities include, but are not limited to, computed tomography, magnetic resonance imaging, ultrasound imaging, X-ray imaging, visible-light photography, microscopic imaging, endoscopic imaging, electronic impendance imaging, mechanic elasticity imaging, optical tomography, and chemical-based molecular imaging.

FIG. 1 also depicts gateway 130. In practice, gateway 130 connects the various and different imaging modalities of a hospital or clinic with the various and different scheduling and/or order filling systems of a hospital or clinic. Thus, gateway 130 is a nexus between multiple systems and imaging modalities of a hospital or clinic and manages the information transfer among them. Gateway 130 may also be connected to administrative databases or other information management systems.

In FIG. 1, scheduling and/or order-filling system 110 sends to gateway 130, for example, scheduling information along with the service settings desired for imaging procedure, facility information, and patient demographic information. Other data is also optionally sent to gateway 130. In the situation where scheduling and/or order-filling system 110 is a so-called "legacy" system, that is, it is an older system that does not conform to DICOM, the data sent to gateway 130 is not in DICOM format. In a legacy situation in a Radiology department of a hospital or clinic, for example, scheduling and/or order-filling system 110 may be a legacy RIS that sends gateway 130 a message in HL-7 rather than in DICOM standard. Other legacy RIS may use proprietary message inputs rather than the DICOM standard.

Referring still to FIG. 1, imaging modality 120 is tasked with a particular imaging procedure by sending a Modality WorkList (MWL) query to gateway 130. The MWL query is in standard DICOM format and seeks out information required by imaging modality 120 in order to perform a given imaging procedure. In the situation where scheduling and/or order-filling system 110 is a legacy system that does not conform to DICOM, a transformation must take place in order to accurately map the nonconforming information sent by scheduling and/or order-filling system 110 to the DICOM format expected by imaging modality 120.

Figure 2:
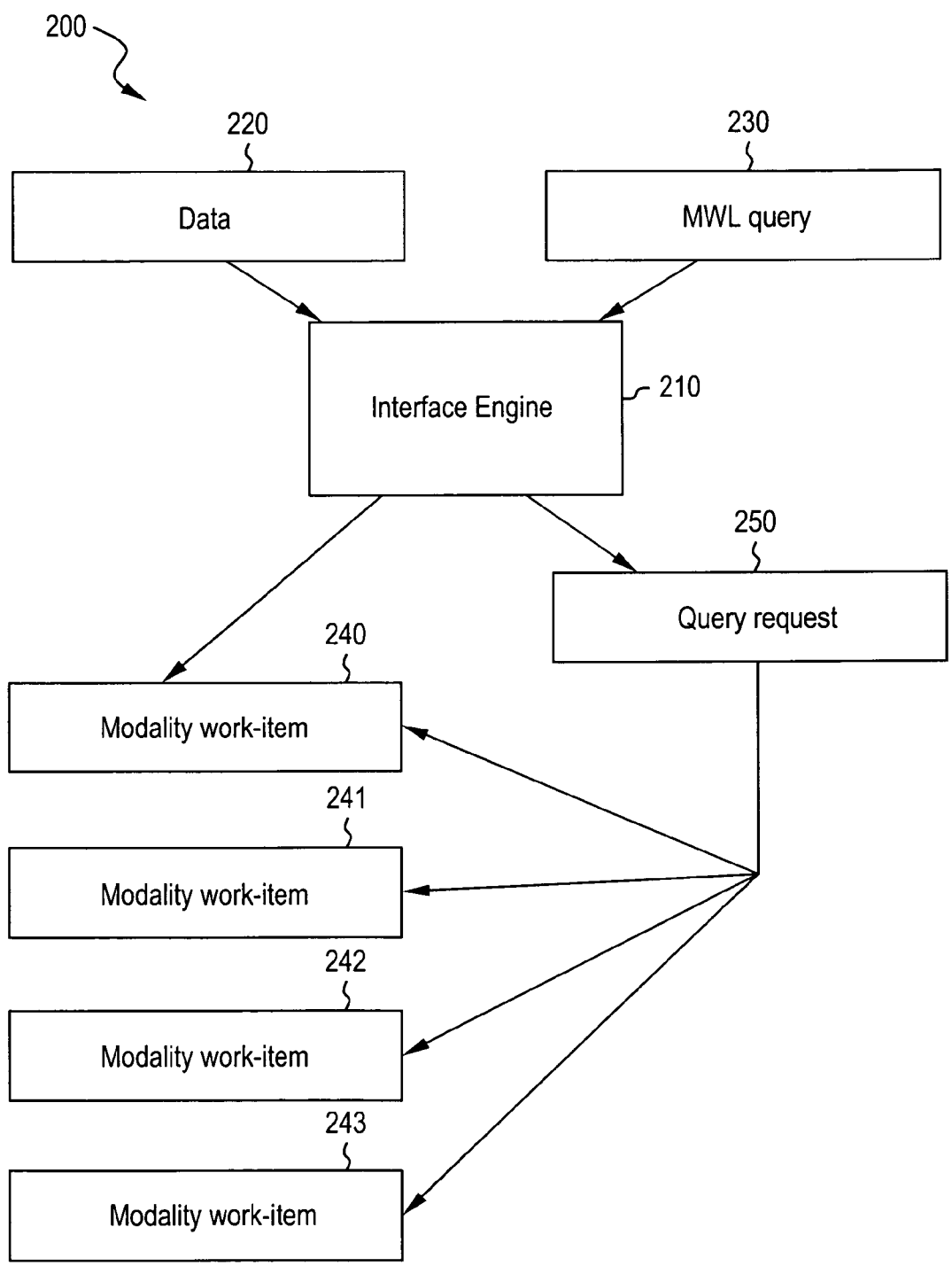
FIG. 2 illustrates a system for the generic interface between modality work list items and a query request according to an embodiment of the present invention.

In certain embodiments, this transformation takes place as illustrated in FIG. 2. FIG. 2 illustrates transformation system 200, including interface engine 210, which in certain embodiments is located within gateway 130 of FIG. 1. In other embodiments, interface engine 210 may be located within scheduling and/or order-filling system 110 or within imaging modality 120. Interface engine 210 may also be located on other systems within the network of a hospital facility provided that interface engine 210 is connected to the scheduling and/or order-filling systems and imaging devices on the network such that interface engine 210 is capable of transforming the data communicated among the scheduling and/or order-filling systems and imaging devices on the network.

Referring still to FIG. 2, data 220 is input data from a scheduling and/or order-filling system, for example scheduling and/or order-filling system 110 of FIG. 1. In the situation where the scheduling and/or order-filling system is a legacy system, data 220 may be nonconforming, either totally or in part, to DICOM. Interface engine 210 accepts data 220 and converts data 220 to a series of modality work-items 240, 241, 242, and 243. Although for the sake of clarity FIG. 2 depicts only four modality work-items, incoming data 220 may contain sufficient information such that interface engine converts data 220 into more or less than four modality work items. Interface engine 210 codes each modality work-item 240, 241, 242, and 243 with a WorkList Category (WLC). A method of coding is described in greater detail below.

Referring still to FIG. 2, interface engine 210 also accepts a Modality WorkList (MWL) query 230 from an imaging device on the network, such as imaging modality 120 depicted in FIG. 1. MWL query 230 typically conforms to DICOM, and therefore in the situation where data 220 is legacy data, MWL query 230 does not correspond directly to data 220. In a legacy situation, interface engine 210 maps MWL query 230 from the preconfigured DICOM query keys onto query request 250. In performing the mapping, interface engine 210 transforms MWL query 230 into query request 250 in such a way that the DICOM query keys map onto WLC queries. A method of mapping is described in greater detail below.

Still referring to FIG. 2, interface engine 210 has coded each modality work-item 240, 241, 242, and 243 with a WLC, and has mapped MWL query 230 onto a WLC query. Thus, previously incompatible data 220 and MWL query 230 are now compatible by virtue of the WLC information they both now contain. Examples of the methods for filling query request 250 from the data contained in modality work-items 240, 241, 242, and 243 are described in more detail below, but generally involves matching the WLC parameters from a given modality work-item with a given query request.

In certain other embodiments, scheduling and/or order-filling system 110 of FIG. 1 does conform to DICOM, as do the various and different imaging devices in the healthcare setting, such as imaging modality 120 of FIG. 1. In certain embodiments, users of scheduling and/or order-filling system 110 seek to customize the data communicated among the systems and devices represented by scheduling and/or order-filling system 110 and imaging modality 120, rather than being constrained to the limited, predefined attributes of DICOM that may have been hard-coded into imaging modality 120. In the situation where the user seeks to transfer customized data, the customized data is then also a type of nonconforming data.

In the situation where a user seeks to transfer customized data, the coding and mapping capabilities of interface engine 210 are particularly useful. Referring again to FIG. 2 but now applying the situation of customizing data, incoming data 220 is again converted to modality work-items 240, 241, 242, and 243. Again, various modality work-items are also coded with WLC parameters. Modality work-item WLC codes may correspond in total or in part to the identity of the attributes of a DICOM query. Since the user in this situation seeks to customize the data transfer, it is likely then some fraction of the modality work-items will not identically correspond with a DICOM attribute and are thus nonconforming to the DICOM standard.

Referring still to FIG. 2 and continuing with the situation where a user seeks to customize data, interface engine 210 accepts MWL query 230 from the various and different imaging devices connected to interface engine 210. Although MWL query 230 is in DICOM format and therefore already compatible with incoming data 220, which is also in DICOM format, interface engine 210 again maps MWL query 230 onto query request 250 such that query request 250 contains WLC parameters. Thus, rather than being bound by the limited, pre-configured attributes of the DICOM standard, interface engine 210 provides for the exchange of data that is not necessarily identical to the pre-configured DICOM attributes. As query request 250 is filled by modality work-items 240, 241, 242, and 243 using the WLC matching scheme, the result is customized data transfer. The coding and mapping capabilities of interface engine 210 allow the user to transfer information specific to the facility or the procedure that was otherwise unavailable using DICOM.

In still another embodiment, the data transferred among scheduling and/or order-filling systems and imaging devices may be extended beyond that certain set of data typically handled by DICOM format data. The transferred data may include certain client communication entity parameters that are commonly available during the network association of a client with a server, for example the client network address. The embodiment is not limited to extended data like network (or IP) addresses, but is flexible enough to incorporate extended data sets that become relevant in future computer and network systems. Extended data sets are another type of nonconforming data.

In another example, the extended data may be the DICOM application entity title, which is data available during network association but is not part of a DICOM query. By accepting the DICOM application entity title as part of the extended data, the standard query keys in a DICOM query request may be used in the standard information model without transformation. Even more generally, certain embodiments take advantage of environmental parameters native to a computer network and system not previously taken advantage of in responding to a conventional MWL query. Parameters not previously taken advantage of in responding to a conventional, industry standard query are another type of nonconforming data.

Again referring to FIG. 2 and in the situation where the system is being used to extend the data transferred among scheduling and/or order-filling systems and imaging devices, interface engine 210 accepts extended data sets in the form of data 220 from scheduling and/or order-filling system 110, or in addition to MWL query 230 from imaging modality 120, or both. Interface engine 210 again performs the coding and mapping functions to modality work-items 240, 241, 242, and 243 and query request 250, respectively, such that each has appropriate WLC parameters. In the situation where the system is being used to extend data, certain of the WLC parameters include the extended data sets supplied from either scheduling and/or order-filling system 110 or imaging modality 120 or both. Again, with WLC parameters common to modality work-items 240, 241, 242, and 243 as well as query request 250, interface engine 210 may efficiently fill query request 250, even with the extended data set of this situation.

In each of the above embodiments and in certain other embodiments, methods of coding, mapping, and querying are used to accurately and efficiently transfer data among the various and different scheduling and/or order-filling systems and imaging devices in a healthcare facility. The coding and mapping functions occur using a method by which information from both DICOM and nonconforming systems are configured as WLC parameters.

WLC may be a generic data type text string, for example. Any piece of information in a scheduled modality work-item may be configured as a WLC parameter. Any piece of information in a standard DICOM MWL query key may be configured as a WLC parameter. And, any type of extended data such as client communication entity parameters may be configured as a WLC parameter.

The method of configuring scheduled modality work-item information, standard DICOM MWL query key information, or extended data may be any number of known mapping models. The value input from the information to be configured may be text or another type of data string. The configured WLC may be text or another type of data string. The input value is configured by matching the input value to a list of possible parameter types supplied to the configuring application. The list of parameter types may be generic or may be site-specific. The list is preferably generic.

The method of querying the coded modality work-items using the mapped query request may be any of a number of known query models. In certain embodiments, the method of querying may employ a query-by-example model. In query-by-example, a complete data set, such as the modality work-items that have been coded with WLC parameters, is compared to an incomplete data set, such as the query request that has been mapped to WLC parameters. The incomplete data set contains enough information that all parts of the complete data set that have data that matches the data from the incomplete set may be located. Once located, the complete data set information may be used to fill in the incomplete data set.

In particular, the incomplete data set may contain the demographic information for a given patient but may be missing information such as the diagnostic procedure code, procedure date, or other pertinent information. When this incomplete data set is compared to the complete data set, all records matching that demographic information for that given patient may be returned. Thus, even though the data in the complete data set may not be arranged in the way sought by the application with the originally incomplete data set, the query-by-example method enables the construction of a complete data set in a new format.

Figure 3:
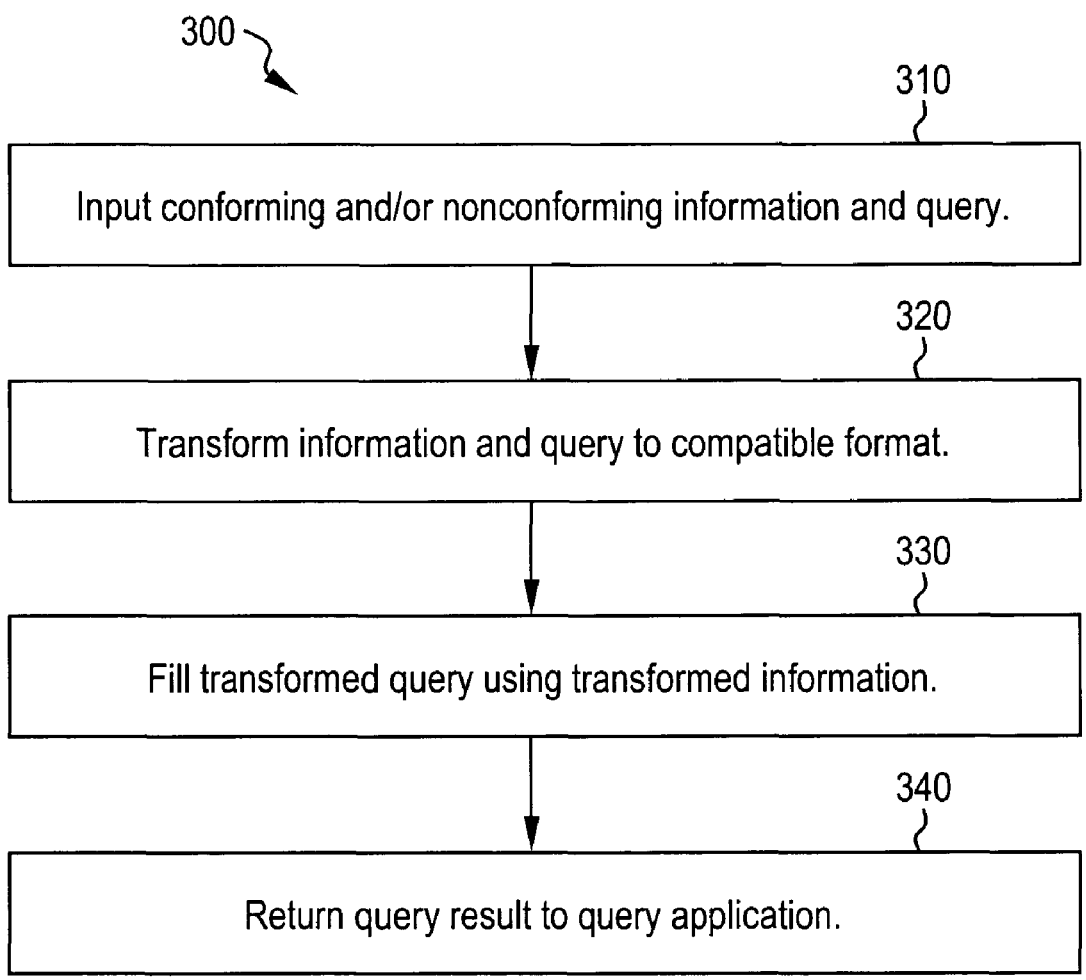
FIG. 3 illustrates a flow diagram for a method for transforming information into a compatible format used in accordance with an embodiment of the present invention.

FIG. 3 illustrates a flow diagram 300 for a method for transforming information into a compatible format used in accordance with an embodiment of the present invention. Information and a query are input to the system in step 310. The information and the query being input may be entirely conforming to DICOM, nonconforming to DICOM, or a mix of both conforming and nonconforming. In step 310, nonconforming information may be in the form of data from a legacy system, or in the form of customized, site-specific data that may in part conform to DICOM, or an extended data set that may include information from the network environment not available using the standard DICOM query format.

In step 320, the information and the query are transformed into a compatible format. The transformation into a compatible format may involve transforming the both the information and the query into a format different from the one in which the information and query are currently formatted. The transformation into a compatible format may involve transforming only the information or the query, or only part of the information and only part of the query. Thus, the compatible format may contain, in whole or in part, elements of the previous formatting of both the information and the query.

In step 330, the query is filled using the information. The query is filled using any model of query-filling, for example query-by-example. The query-filling model may be iterative in nature.

In step 340, the query is returned to the query application. The filled query may be reformatted into the original format of the query from step 310, or it may be left in whole or in part in the new format created in step 320. Returning the filled query enables the query application to perform the request function, such as diagnostic imaging of a given patient according to the procedure codes and facility-specific settings supplied by the information management system.

EXAMPLE 1

As one example, a clinic has a legacy RIS in its Radiology department. A staff member seeks to schedule a Computed Tomography (CT) imaging procedure for a newly admitted patient. The staff member interacts with the RIS to create a procedure and schedule specific to the patient. The RIS communicates the scheduling information to the gateway in a proprietary data format specific to the legacy RIS.

When the gateway receives the scheduling information, the data fields in the scheduling information are configured to be part of a WLC. For example, the field "procedure requesting department" contains the relevant data for seeking a CT scan for the Radiology department in the proprietary RIS format. The gateway codes the "procedure requesting department" data into a WLC parameter that is generic for that data field type, such as "CT Center". The coding process configures all of the other data fields in the scheduling information into other corresponding WLC parameters.

An imaging modality queries the gateway in DICOM format with a specific MWL query. The "modality" field of the DICOM query is filled with the specific modality code, "CT". A list of value mapping on the gateway application defines that the value "CT" of the field "modality" in a DICOM query matches to the values "CT Center" of the WLC. The gateway fills the entire query of the imaging modality using the list of value mapping and the query-by-example model.

The imaging modality then receives from the gateway a DICOM-compliant response to the query with the patient data, schedule, procedure codes, and other relevant information. The CT procedure is successfully scheduled.

It is understood that in the above descriptions, a user in any of the embodiments of the apparatus, method, and system may be a physician, radiologist or other healthcare professional or staff member in a hospital or clinic department, a member of the information technology staff of a healthcare facility, or any other individual who implements, maintains, services, or otherwise interacts with the computer networks and systems of a given healthcare facility.

Thus, certain embodiments of the system and method provide customizable workflow management in a healthcare setting and provide for the capture of nonconforming information. Certain embodiments of the system and method provide for integrating legacy systems into an industry standard information format, such as DICOM, with a generic interface rather than a system specific coding solution. Certain embodiments of the system and method provide for optimizing a workflow among conforming systems of a healthcare facility by generically reconfiguring the query system of DICOM, or other industry standard information formats.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. An information interface system comprising:
a diagnostic device that transmits a query for information regarding a procedure to be performed using the diagnostic device, the query conforming to a Digital Imaging and Communications in Medicine (DICOM) format for information transfer;
an order scheduling system that transmits data regarding the procedure to be performed using the diagnostic device, the data conforming to an HL7 format for information transfer, which differs from said DICOM format; and
a gateway system comprising an interface engine, wherein the gateway system receives the query transmitted by the diagnostic device and the data transmitted by the order scheduling system,
wherein the interface engine:
associates data transmitted by the order scheduling system with one or more worklist category parameters that do not conform entirely to either of the DICOM and HL7 formats for transferring information,
associates the query transmitted by the diagnostic device with one or more of the worklist category parameters that do not conform entirely to either of the DICOM and HL7 formats for transferring information, and
matches the one or more worklist category parameters associated with the query transmitted by the diagnostic device with the one or more worklist category parameters associated with the data transmitted by the order scheduling system, thereby matching information sought by the query transmitted by the diagnostic device with data transmitted by the order scheduling system, and
wherein the gateway system provides a response to the query transmitted by the diagnostic device, the response including data transmitted by the order scheduling system that was matched using the interface engine, the response conforming to the DICOM format for information transfer.

2. The system of claim 1, wherein the interface engine converts data transmitted by the order scheduling system into one or more modality work items, each modality work item being coded with a worklist category parameter.

3. The system of claim 1, wherein the diagnostic device is an imaging modality.

4. The system of claim 1, wherein the order scheduling system is selected from the group consisting of a Radiology Information System (RIS), a Hospital Information System (HIS), a Clinical Information System (CIS), and a Picture Archive and Communication System (PACS).

5. The system of claim 2, wherein the interface engine maps a client communication entity parameter to a modality work-item.

6. The system of claim 5, wherein the client communication entity parameter is a network address of the diagnostic device.

7. The system of claim 1, wherein the interface engine maps the query transmitted by the diagnostic device to one or more modality work items, each modality work item being coded with a worklist category parameter.

8. The system of claim 1, wherein the diagnostic device and the order scheduling system are within a healthcare setting.

9. An information interface system comprising:

a gateway system comprising an interface engine, wherein the gateway system receives a query from a diagnostic device regarding a procedure to be performed using a diagnostic device, the query conforming to a Digital Imaging and Communications in Medicine (DICOM) format for information transfer, and wherein the gateway system receives data regarding the procedure to be performed using the diagnostic device from a scheduling system, the data conforming to an HL7 format for information transfer which differs from said DICOM format, wherein the interface engine:

associates the received data with one or more worklist category parameters that do not conform entirely to either of the DICOM and HL7 formats for transferring information, associates the query with one or more of the worklist category parameters that do not conform entirely to either of the DICOM and HL7 formats for transferring information, and matches the one or more worklist category parameters associated with the query with the one or more worklist category parameters associated with the received data, thereby matching information sought by the query with received data, and wherein the gateway system provides a response to the query, the response including received data that was matched using the interface engine, the response conforming to the DICOM format for information transfer.

10. The system of claim 9, wherein the interface engine converts received data into one or more modality work items, each modality work item being coded with a worklist category parameter.

11. The system of claim 9, wherein the diagnostic device is an imaging modality.

12. The system of claim 9, wherein the data is transmitted to the gateway system from an order scheduling system comprising at least one of a Radiology Information System (RIS), a Hospital Information System (HIS), a Clinical Information System (CIS), and a Picture Archive and Communication System (PACS).

13. The system of claim 9, wherein the interface engine maps the query to one or more modality work items, each modality work item being coded with a worklist category parameter.

* * * * *